United States Patent [19]

Davis

[11] Patent Number: 5,098,402
[45] Date of Patent: Mar. 24, 1992

[54] RETRACTABLE HYPODERMIC SYRINGE

[76] Inventor: Lynn E. Davis, 5511 Spanish Oak, Houston, Tex. 77066

[21] Appl. No.: 527,385

[22] Filed: May 23, 1990

[51] Int. Cl.$^5$ .............................................. A61M 5/32
[52] U.S. Cl. ...................................... 604/195; 604/110
[58] Field of Search .............. 604/195, 110, 263, 192, 604/187, 242, 241, 240

[56] References Cited

U.S. PATENT DOCUMENTS

| 4,883,471 | 11/1989 | Braginetz et al. | 604/195 |
| 4,932,939 | 6/1990 | Magre et al. | 604/110 |
| 4,950,241 | 8/1990 | Ranford | 604/110 |

Primary Examiner—John D. Yasko
Attorney, Agent, or Firm—James L. Jackson

[57] ABSTRACT

A retractable hypodermic syringe is provided having a syringe body forming a barrel at one end and a tubular needle connector at the opposite end which surrounds a needle support passage and forms cam surfaces and locking recesses at the end portion of the needle connector. A needle support element is positionable within the needle support passage and has cam projections which are extendible through grooves defined along the needle support passage to bring the cam projections into registry with the cam surfaces. A plunger which is receivable within the syringe barrel is provided with an elongated projection that serves both as a piston support for a resilient piston carried thereby and as a needle support actuator which is movable into releasably interlocked relation with the needle support element thus enabling the plunger to impart both rotational and linear movement to the needle support element for its locking, unlocking and retracted positions relative to the syringe body. The plunger is movable to a position locking the forward portion of the plunger, the piston and the needle support element with a syringe needle affixed thereto at an enclosed and protected position within the syringe barrel. The plunger includes a frangible section enabling the rear portion of the plunger to be broken away after locking of the forward portion of the piston has been accomplished.

20 Claims, 2 Drawing Sheets

RETRACTABLE HYPODERMIC SYRINGE

FIELD OF THE INVENTION

This invention relates generally to hypodermic syringes such are utilized for injection of medicament into the body tissues of human and animal patients. More specifically, this invention relates to a hypodermic syringe having a plunger, piston and needle support structure that permits retraction of the needle support and its needle into the barrel of the syringe to prevent the possibility of inadvertent needle pricks and which incorporates a frangible plunger that may be broken away to prevent subsequent actuation of the needle to its operative position.

BACKGROUND OF THE INVENTION

In hospitals, nursing home facilities and the like, injection of medicament into the body tissues of patients is done on a daily basis. Typical hypodermic syringes are provided with a barrel having a needle that is fixed or removably attached at one end thereof. A plunger typically having an elastomeric piston is movable within the barrel to load the barrel with liquid medicament by suction as the plunger and piston are moved within the barrel in a direction away from the needle. After the needle has penetrated the body tissues of the patient, as the direction of movement of the plunger and piston are reversed and the piston is forced toward the needle, medicament contained within the barrel will be injected through the needle into the body tissues.

After hypodermic syringes have been used in this manner, those syringes that are disposable present a significant problem to the hospital or nursing home staff because the possibility of inadvertent needle pricks subject nursing personnel to the possibility of cross-contamination by virile or bacterial contaminants that might be present on the needle after its use. In an effort to avoid the possibility of inadvertent needle pricks special waste containers are often provided at hospital facilities into which the used disposable hypodermic syringes are placed. These containers and the syringes contained therein are then disposed of in a specifically organized manner to insure against the possibility of inadvertent infectious contamination of nursing personnel. Further, refuse handlers and other persons who might inadvertently come into contact with the used hypodermic syringes are also subject to the same hazards. Often times the needles themselves are bent over so as to minimize the possibility of inadvertent needle pricks and to preclude the possibility of subsequent use of disposable hypodermic syringes.

In emergency conditions, such as during use by paramedics in ambulances during transportation of patients to trauma centers, various medicaments are injected into patients by paramedics under the direction of medical staff personnel. To minimize the possibility of inadvertent pin pricks by used hypodermic syringes and to enhance the speed of the emergency care being accomplished, the paramedic staff will often toss used hypodermic syringes onto the floor of the emergency vehicle such that the syringes are out of the way of both the patient and the paramedics. After the emergency has ended and these syringes are manually recovered for disposal, there is the possibility that inadvertent needle pricks will occur. It is of course desirable to provide a suitable facility for protecting nursing personnel, paramedics and other persons from the hazards of inadvertent needle pricks as they go about their daily tasks.

It is known that in the past hypodermic syringes have been disposed of by dumping the same, together with other hospital refuse at certain locations in the ocean. Not only is this hazardous to the marine environment because of the presence of the hypodermic syringes and medical contaminates in the ocean and the possibility of cross-contamination that might occur, it is well known that used disposable syringes and other medical refuse tends to wash up on the beaches where it becomes a hazard to persons, especially children, that might be present at the beach.

It is desirable, therefore, to provide a hypodermic syringe that includes a facility for rendering the needle thereof to a protected, completely encapsulated condition such that it can not possibly cause an inadvertent needle prick at any time during its handling or during its disposal. It is desirable to provide a hypodermic syringe having the capability of retracting the needle to a position inside the barrel of the syringe and locking the needle in its retracted position so that the needle of the hypodermic syringe is always enclosed after its use, thus precluding the possibility that the needle might cause an accidental needle prick as the syringe is subsequently handled. It is also desirable to provide a hypodermic syringe of the disposable type that is provided with facility for rendering it completely inoperative such that it can not be subsequently used.

THE PRIOR ART

Various types of hypodermic syringes having retractable needles have been developed such as evidenced by Gloyer et al. U.S. Pat. No. 4,747,830 and Haining U.S. Pat. No. 4,790,822. In addition to being provided with retractable needle carriers, the syringes of Gloyer, et al. and Haining are also shown to be provided with frangible plungers that are broken manually to render the syringes inoperative for further use.

SUMMARY OF THE INVENTION

It is a principle of the present invention to provide a novel retractable hypodermic syringe having a needle support that is capable of being positively locked in operative assembly with the barrel structure thereof and which is capable of being easily and simply unlocked and retracted to a safe position within the barrel where the needle is withdrawn to an enclosed and protected position preventing the possibility of inadvertent needle pricks.

It is also a feature of this invention to provide a novel retractable hypodermic syringe having a frangible plunger that may be manually broken after the syringe has been used and the needle has been retracted and locked safely within the syringe barrel to thus render the syringe inoperative for further use.

It is an even further feature of this invention to provide a novel retractable syringe including internal locking means that is mechanically interactive with a portion of the plunger to achieve positive locking of the needle and needle support at a position within the barrel of the syringe such that the needle is incapable of causing an inadvertent needle prick.

It is another feature of this invention to provide a novel retractable needle mechanism for hypodermic syringes which incorporates a needle protector that is frictionally secured in place or threaded into place with respect to the body of the syringe to thus provide the needle with protection against inadvertent needle pricks prior to use thereof.

Briefly, the invention is directed to a retractable hypodermic syringe mechanism including a syringe body forming a cylindrical barrel, which barrel receives a plunger in movable relation therein with an elastomeric piston being disposed in assembly with the plunger and having sealing relation with the internal cylindrical surface of the barrel. The distal end of the syringe body defines at least one and preferably a pair of opposed cam surfaces and forms a pair of internal longitudinal slots. A needle support is provided, having a hypodermic needle affixed thereto or capable of being assembled therewith by means of any suitable type of connection. The needle support is provided with a pair of opposed bosses or projections that are of a dimension and location to be extended through the parallel grooves from within the cylinder barrel such that the opposed bosses are positioned in registry with the cam surfaces. The needle support is further provided with the capability of establishing a sealing engagement internally of the syringe body and defines a receptacle within which is received a connecting and actuating projection extending from the plunger such that a non-rotatable relationship is established between the plunger and the needle support. The needle support is positively seated with respect to the body structure of the syringe upon its rotation within the syringe body which is induced by rotation of the plunger within the syringe barrel. The connection between the plunger and the needle support is capable of separation upon application of linear force to the plunger with the needle carrier in its locked position relative to the syringe body. After use of the syringe has occurred and its disposal is desired, the plunger is rotated in an unlocking direction, through its driving connection with the needle support element, to rotate the needle support element to a position aligning the opposed bosses or cam projections with the parallel internal grooves of the syringe body. In this position, linear movement of the plunger in a direction away from the needle support will thus induce retracting movement of the needle support and needle to thus retract the needle to a protected position within the syringe barrel. The plunger and syringe barrel are also adapted for locking a portion of the plunger, the piston and needle support in a safe retracted position within the syringe barrel and for breaking away the operating portion of the plunger such that the syringe is rendered inoperative for further use.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF PREFERRED EMBODIMENT

Figure 1:
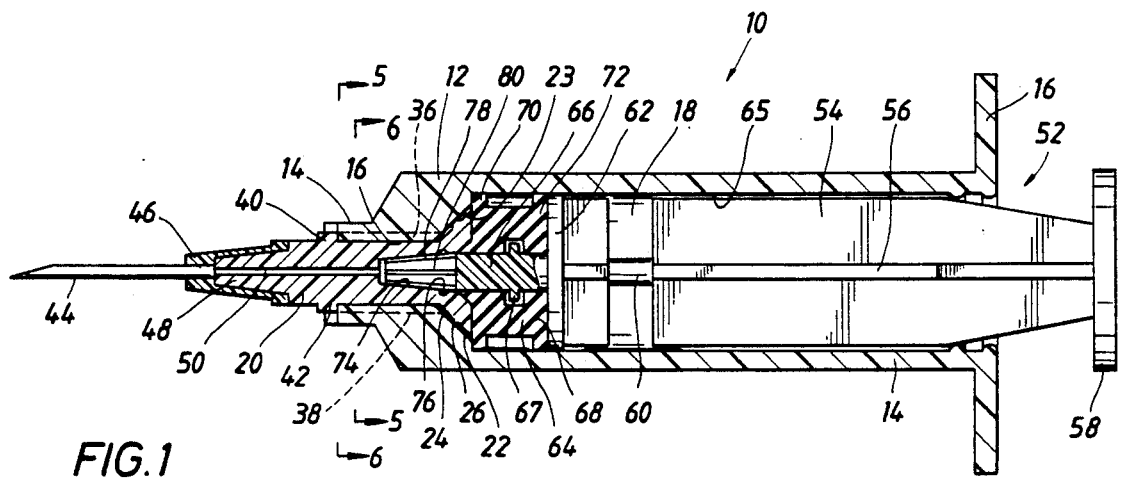
FIG. 1 is a sectional view of a retractable syringe constructed in accordance with the present invention and illustrates the syringe with the hypodermic needle in position for use and the plunger and piston in a position in readiness for loading or for retraction of the needle.
Figure 2:
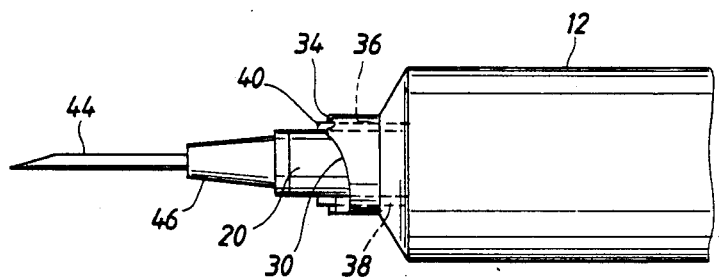
FIG. 2 is a fragmentary elevational view of the retractable hypodermic syringe of FIG. 1, illustrating the needle and needle carrier in the position shown in FIG. 1 and showing cam surfaces for positioning and locking the needle carrier in its operative position.
Figure 3:
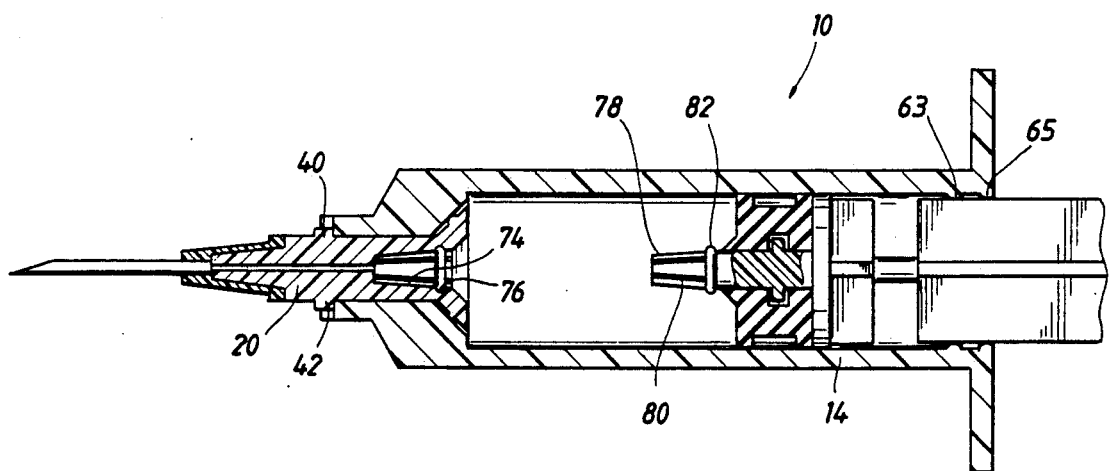
FIG. 3 is a sectional view similar to that of FIG. 1 and illustrating the plunger and piston being separated from the needle carrier and being retracted such as would occur during loading of the barrel with medicament or dispensing of the medicament to the patient.

Referring now to the drawings and first to FIG. 1, a retractable hypodermic syringe constructed in accordance with the present invention is illustrated generally at 10 and comprises a body structure 12 forming an elongate cylindrical barrel 14 and a transverse flange 16 at one end of the barrel. At its forward end the body structure 12 forms a tubular extension 15 in the form of a cylindrical sleeve which is disposed concentrically about a passage 16 that extends through the body 12 and into the internal chamber 18 defined by the barrel 14.

A needle support element 20 is normally positioned within the passage 16 and includes a rear end portion 22 which is sealed with respect to the body 12. As shown in FIG. 1, the rear end portion 22 of the needle support element is of tapered configuration forming a frustoconical surface 24. The tapered rear portion of the needle support element also defines a circular sealing rib 26 which is disposed in sealing engagement with the internal tapered sealing surface 23 of the needle body. Alternatively, other structural interrelationships between the needle support element and the body 12 may be employed in order to accomplish efficient sealing between these parts.

Figure 4:
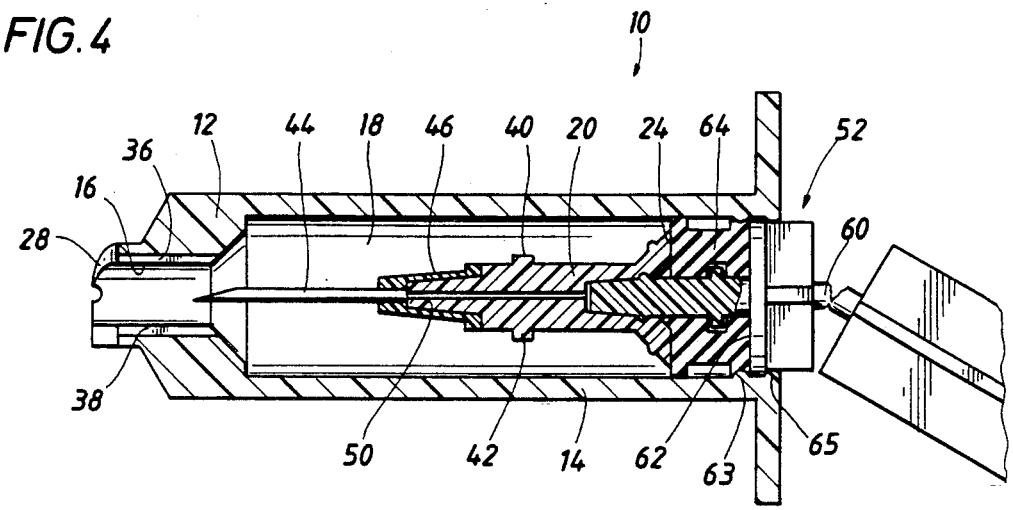
FIG. 4 is a sectional view similar to that of FIG. 1 and illustrating the retracted and protected position of the needle carrier and needle and further showing breaking of the plunger.
Figure 5:
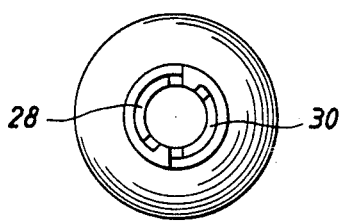
FIG. 5 is a sectional view taken along the line 5—5 of FIG. 1.
Figure 6:
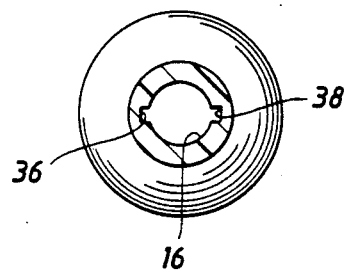
FIG. 6 is a sectional view taken along line 6—6 of FIG. 1.
Figure 7:
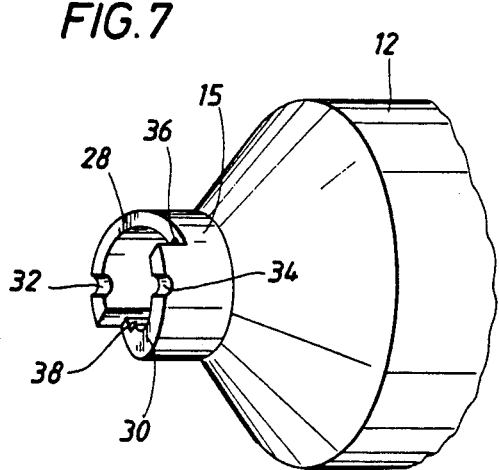
FIG. 7 is a partial isometric illustration showing the forward part of the syringe of FIG. 1 and showing the cam surfaces and locking recesses of the tubular connector thereof.

The needle support element 20 is capable of being locked at the position shown in FIG. 1 and is capable of being released from its locked condition such that it may be moved to a retracted position within the chamber 18 of the barrel in the manner shown in FIG. 4. Positioning and locking of the needle support element relative to the body structure 12 is accomplished by means of a camming and locking mechanism established by interactive mechanical relationship between the needle support element 20 and the tubular extension 14 of the body 12. As shown in the various drawings and especially evident from the isometric illustration of FIG. 7, the tubular extension 15 of the body 12 forms a pair of opposed tapered cam surfaces 28 and 30 and a pair of opposed locking recesses or depressions 32 and 34. The body 12 is formed to define a pair of opposed internal parallel longitudinal slots 36 and 38 that open to the passage 16 along the length of the passage and extend from the chamber 18 through the body 12 to the free end of the tubular extension. The needle support element 20 defines a pair of opposed cam projections 40 and 42 which are of a dimension enabling passage of the same through the opposed bosses forming slots 36 and 38.

For locking the needle support element 20 relative to the body structure 12 in the manner shown in FIG. 1, the needle support element is extended from the chamber 18 within the tubular barrel 14 through the passage 16 with the opposed cam projections 40 and 42 disposed within the respective internal slots 36 and 38. After predetermined movement of the needle support element 20 in this manner, the opposed cam projections become positioned in registry with the tapered opposed cam surfaces 28 and 30. The needle support element 20 is then rotated approximately 90°, causing the cam projections to react against the tapered cam surfaces 28 and 30 thus imparting further linear movement of the needle support element forwardly through the passage 16 thus moving its tapered trailing end portion 22 into sealing engagement with the sealing element 26 to thus establish a positive seal between the needle support element and the body structure 12. After the cam projections 40 and 42 have been rotated approximately 90° they reach the respective locking recesses 32 and 34 and snap into place within the locking recesses, thereby firmly securing the needle support element in immovable firmly supported relation with respect to the body 12 and its barrel 14. In this condition, a hypodermic needle 44 carried by a needle adapter 46 and fitted to a tapered projecting portion 48 of the needle support element, may be used to penetrate the tissues of the patient for injection of medicament therein. When locked in the position shown in FIG. 1, the needle support element can not be inadvertently retracted by the force of tissue resistance as the syringe needle is forced into the body tissue of the patient in preparation for injection of medicament into the body tissue.

Within the barrel 14 of the syringe is movably positioned a plunger illustrated generally at 52 which may be formed by intersecting webs 54 and 56 of polymer material which may be molded in integral assembly to provide a light-weight plunger having sufficient structural integrity for loading the barrel with medicament and dispensing the medicament through the passage 50 and hollow needle 54 into the body tissues of the patient. The plunger 52 is also of sufficient structural integrity for imparting rotational movement to the needle support element 20 as will be described hereinbelow for the purpose of locking and unlocking the needle support element relative to the body structure 12. The plunger 52 is provided with an end flange 58 which is typically engaged by the thumb of the user while the transverse flange 16 is engaged by the fingers of the user in order to enable the plunger to be forced into the barrel for the purpose of expelling the medicament from the barrel through the passage 50. Intermediate the extremities of the plunger 52 the webs 54 and 56 are broken away and a frangible section 60 is provided which enables the trailing end of the plunger to be broken away in the manner shown in FIG. 4. The frangible section 60 may be scored to insure that it will break at the proper location; however, it is of appropriate dimension for sufficient structural integrity to provide for transmission of locking and unlocking forces to the needle support element 20 and to impart linear force to the plunger.

At the forward end of the plunger, there is provided a transverse support or abutment flange 62 which is of a dimension less than that of the internal cylindrical surface 65 of the barrel 14. The flange 62 provides abutting support for a resilient piston 64 which is received about a piston connector 66 which is integral with the plunger and extends forwardly of the piston abutment flange 62. The connector 66 forms an intermediate enlargement 67 which is received within an internal recess of the piston thus serving to secure the piston to the plunger and to permit relative rotation of the piston and plunger. The piston also defines a pair of spaced external sealing lands 70 and 72 that establish sealing engagement with the cylindrical internal wall 64 of the syringe barrel. Thus, as the plunger 52 is movable linearly within the barrel the piston lands 70 and 72 maintain sealed engagement with the cylindrical surface 64 and thereby provide the plunger with the capability of imparting significant hydraulic pressure to the liquid medicament which may be contained within the syringe barrel.

It is desirable to provide a releasable connection between the plunger and the needle support element to thus enable the plunger to be rotatably moved for its positioning and locking relationship with the body 12 of the syringe and to enable the plunger to be unlocked by rotational movement and retracted linearly to a safe position within the barrel after the syringe has served its purpose. According to the principles of this invention, one suitable means for accomplishing this feature may incorporate the structure illustrated particularly in FIG. 1 where the needle support element 20 is shown to define a tapered internal receptacle 74 which is disposed in registry with the dispensing passage 50 and which further defines an internal circular locking groove 76. The receptacle 74 forms internal ridges and grooves 75. A forward portion of the piston connector 66 defines a tapered needle support actuator 78 defining external ribs 80 along a significant portion of the length thereof for establishment of a non-rotatable relation with the needle support actuator of the plunger. The needle support actuator 78 defines an external transverse circular locking ridge or rib 82 which is receivable in interengaging locking relation within the internal groove 76 to thus establish a releasable, locking relation therewith. The locking ridge 82 also serves as a retainer for the piston 64, which, due to its flexible nature, is easily forced over the locking ridge to its seated and retained relationship with the piston connector. Additionally, when the needle support element 20 is in assembly with the needle support actuator 78 of the piston connector 66, the needle support element also serves a retaining function to secure the piston in assembly with the piston connector. The internal receptacle 74 may define internal ridges and grooves along its tapered internal surface to establish a non-rotational relationship with respect to the needle support actuator projection 78. The internal and external ridges and grooves interact as the plunger 52 is rotated to thus enable the rotational force of the plunger to be imparted to the needle support element 20 such that it may be rotated for locking or unlocking relative to the tubular projection 14 of the syringe body 12. Also, if desired the needle support actuator 78 may have a frictional fit within the receptacle 74 which has sufficient force transmitting integrity to rotate the needle support element and to move it in linear manner.

Figure 8:
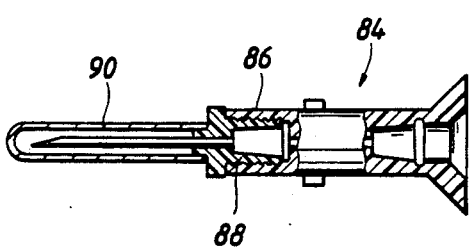
FIG. 8 is a partial sectional view of an alternative needle support element which includes an internally threaded forward end which threadedly receives a needle protector.

As is evident from FIG. 8 an alternative embodiment of the needle support element is shown generally at 84 which defines an internally threaded tubular forward projection 86 which receives the externally threaded connector portion 88 of a needle protector 90. The needle support element 84 is otherwise of similar construction and operation as compared to the needle support element 20.

OPERATION

Typically, the retractable syringe 10 will be supplied with the needle support element 20 perhaps with a needle 44 and needle adapter being received by the tapered needle support projection 50 in the manner shown in FIG. 4. Alternatively, a suitable needle for the intended injection together with its needle adapter may be assembled to the needle support element after the needle support element has been locked in operative position relative to the body structure of the syringe. If the needle 44 and its adapter are not present, obviously there would be no danger of a needle prick prior to injection of the patient. In this case, the needle support element 20 may be locked at its operative position in the manner shown in FIG. 1 in readiness for application of a needle and needle adapter thereto. This would enable nursing personnel to select the proper needle for the intended injection and simply connect it to the needle support element of the syringe by a simple compression fit. If the needle support element 20 is locked in place on the syringe body, the plunger 52 may be positioned as shown in FIG. 1, with the needle support actuator locked within the tapered receptacle 74 to thus minimize the overall packaged length of the retractable syringe.

If the syringe is delivered in the condition shown in FIG. 4, the plunger 52 will be moved forwardly within the barrel 14 thus extending the needle support through the passage 16 and extending the cam projections 40 and 42 through the opposed internal slots 36 and 38 to a location clear of the longitudinal slots and in registry with the cam surfaces 28 and 30 of the tubular extension 15 of the syringe body. When the cam projections 40 and 42 have reached the tapered cam surfaces 28 and 30, the plunger is rotated in a direction to cause the cam projections to ride up the tapered cam surfaces. This urges the needle support element to move both rotationally and linearly further into the passage 16 until the tapered trailing extremity 24 thereof engages the circular seal and establishes a sealed relationship with respect to the body 12 of the syringe. Rotation of the needle support element continues until such time as the cam projections 40 and 42 reach and become seated in locked relation within the respective locking recesses 32 and 34. In this position the needle support element is in locked relation with the syringe barrel.

With the needle support 20 locked in this manner the plunger 52 is then retracted within the chamber 18 of the barrel, thus imparting a linear force to the piston connector 56 and its needle support actuator 78. When this linear force becomes sufficiently great the circular ridge 82 will be forcibly withdrawn from the internal circular receptacle 76 thus releasing the plunger from the needle support 20. The plunger is then moved in a retracting direction away from the needle support to develop a suction within the chamber 18 which forces medicament through the needle and through passage 50 into the chamber 18. After the chamber 18 has been loaded to the extent appropriate with liquid medicament the syringe barrel is manipulated to cause penetration of the needle 44 into the tissues of the patient. The plunger is then moved in a forward dispensing direction to inject the liquid medicament through the passage 50 and through the needle 44 into the patient. Plunger movement in the dispensing direction is complete when the tapered needle support actuator 78 becomes fully seated within the tapered internal receptacle 74 of the needle support and the circular locking ridge 82 of the needle support actuator 78 is forced into seated, locking relation within the internal circular groove 76 of the needle support element. In this condition, the plunger is fully locked to the needle support element and is capable of imparting linear force thereto in either direction and through the interacting ridges and grooves of the needle support actuator 78 and the inner wall surfaces of the receptacle 74 is capable of imparting rotational force to the needle support element as well.

The plunger 52 is rotated in the unlocking direction, imparting rotational movement to the needle support element to release the cam projections 40 and 42 from the locking recesses 32 and 34 and to enable the cam projections to traverse the inclined cam surfaces 28 and 30 and become positioned in registry with the internal parallel slots 36 and 38. When this position has been accomplished, the plunger is then further retracted inducing linear movement to the needle support element to retract it from within the passage 16 of the syringe body to the fully retracted position shown in FIG. 4. In the fully retracted position the circular transverse flexible flange 62 of the plunger will be positioned in locked relation between the spaced internal locking ribs 63 and 65 of the syringe barrel 14. The flange 62 is yieldable to permit it to be forced past the first internal rib 63 into the receptacle between the ribs 63 and 65. In this position, the forward portion of the plunger is positively locked relative to the barrel 14 of the syringe and the needle carrier 20 with its needle adapter and needle are completely contained in safe position within the chamber 18 of the syringe barrel. The yieldable flexible character of the flange 62 enables it and the resilient piston to be forced past the outer locking rib 65 for complete separation of the plunger assembly from the syringe barrel if desired.

To render the syringe further inoperative, a transverse force is then applied to the free end portion of the plunger thereby causing the frangible section 60 thereof to fail so that it can be removed. In this condition, the forward portion of the plunger, the piston 64, the needle support 20 and the needle 44 are locked in substantially immovable protected relation within the syringe barrel and the syringe itself is rendered inoperative by breaking of the frangible section 60. The disposable syringe then may be safely handled without the possibility of an inadvertent needle prick occurring and may be disposed of without creating danger to nursing personnel or refuse handling personnel.

In view of the forgoing, it is seen that the present invention is well adapted to attain all of the features hereinabove set forth together with other objects and features which are inherent in the apparatus itself.

While the foregoing is directed to the preferred embodiment it is recognized that the apparatus may take on various other embodiments within the spirit and scope of the invention, the scope hereof is determined by the claims which follow.

What is claimed is:

1. A retractable hypodermic syringe comprising:
   (a) a syringe body forming a syringe barrel having a tubular needle connector at one end thereof, said needle connector having cam surface means and needle support locking means at the free extremity thereof, said syringe body further forming a needle support passage having at least one longitudinal internal slot extending along said needle support passage and terminating within said syringe barrel;
   (b) a needle support element being positionable within said needle support passage and having at least one cam projection thereon being enabled to traverse said longitudinal internal slot and to be positioned in registry with said cam surface means, said needle support element forming a connector for receiving a syringe needle adapter, upon rotation of said needle support in one direction relative to said cam surface means said cam projection reacting with said cam surface means to impart linear driving movement to said needle support element to a locked position where said cam projection establishes locking engagement with said needle support locking means, upon rotation of needle support element in the opposite direction relative to said cam surface means, said needle support element being unlocked; and
   (c) a medicament injecting plunger being movable within said syringe barrel and supporting a resilient piston in sealed relation within said syringe barrel, said plunger having a needle support actuator extending forwardly of said resilient piston and disposed for releasable substantially non-rotatable driving relation with said needle support element and being operative upon selective rotational and linear movement of said plunger relative to said syringe body to impart locking, unlocking and camming rotation of said needle support element and to move said needle support element to positions exposing said needle support element forwardly of said syringe body and retracting said needle support and a hypodermic needle and needle adapter in assembly therewith to a safe protected position within said syringe barrel.

2. The retractable hypodermic syringe of claim 1, wherein:
   (a) said tubular needle connector is of generally cylindrical form and is disposed concentrically about said needle support passage; and
   (b) said cam surface means forms a portion of the end surface of said tubular needle connector.

3. The retractable hypodermic syringe of claim 2, wherein:
   said tubular needle connector forms locking recess means at the end portion thereof, said locking recess means receiving said cam projection of said needle support element to releasably lock said needle support element in substantially immovable relation with said syringe body.

4. The retractable hypodermic syringe of claim 1, wherein:
   said syringe body and said needle support element form interactive sealing means establishing a seal upon positioning and locking of said needle support element relative to said tubular needle connector of said syringe body.

5. The retractable hypodermic syringe of claim 1, wherein:
   (a) said needle support actuator of said plunger being a tapered projection extending from said plunger and having locking means thereon; and
   (b) said needle support element forming a connection receptacle having internal locking means receiving said locking means of said needle support actuator in releasable locked relation therein.

6. The retractable hypodermic syringe of claim 5, wherein said needle support actuator and said connection receptacle form ridges and grooves that establish a non-rotatable relation between said needle support actuator and said needle support element to enable locking and unlocking rotation of said needle support element by selective rotation of said plunger.

7. The retractable hypodermic syringe of claim 1, wherein:
   (a) said needle support element defines an internal locking receptacle having an internal circular locking groove formed therein;
   (b) said needle support actuator forms an external circular rib that is releasably engageable within said internal circular locking groove to thus establish an interlocking relationship between said needle support actuator and said needle support element that resists predetermined linear force therebetween and enables releasing of said locking connection between said needle support actuator and said needle support element upon application of manual force exceeding said predetermined force.

8. The retractable hypodermic syringe of claim 5, further comprising:
   a piston connection extending forwardly from said plunger and receiving said piston in interlocking assembly therewith, said piston connector forming said needle support actuator at the forward free extremity thereof.

9. The retractable hypodermic syringe of claim 8, wherein:
   (a) said plunger forms a circular piston abutment member; and
   (b) said syringe barrel forms a pair of spaced internal ribs receiving said piston abutment member in locked relation therebetween upon movement of said plunger to its fully retracted and locked position, thus securely locking said piston, needle support and needle in protected relation within said syringe barrel.

10. The retractable hypodermic syringe of claim 9, wherein:
    said plunger forms a frangible section 60 intermediate the extremities thereof which is manually fracturable at the locked position of said piston abutment member to thus lock a forward portion of said plunger, said piston and said needle support element and a needle and needle adapter supported thereby in safe, fully enclosed position within said syringe barrel.

11. A retractable hypodermic syringe comprising:
    (a) a syringe body forming a syringe barrel and having a tubular needle connector at one end thereof forming a needle support passage extending forwardly from said syringe barrel, said tubular needle connector further forming cam surface means and needle support locking means and forming internal longitudinal needle support guide means extending along said needle support passage and terminating at said cam surface means;

(b) a needle support element being movably disposed within said syringe barrel and being positionable within said needle support passage in sealed relation with said syringe body and being retractable to a secured position within said syringe barrel, said needle support element defining cam projection means for camming reaction with said cam surface means to impart linear locking movement to said needle support element;

(c) locking means releasably locking said needle support element within said needle support passage and being releasable to permit retraction of said needle support element to said secured position;

(d) a plunger being movable within said syringe barrel and having needle support actuator means thereon for establishing releasable rotational driving connection with said needle support element for locking and unlocking said locking means; and (e) a resilient piston being supported by said plunger and establishing a sealed relationship between said plunger and said syringe barrel.

12. The retractable hypodermic syringe of claim 11, wherein said locking means comprises:

(a) cam surface means being defined by said syringe body; and (b) cam means being defined by said needle support element and having camming and locking engagement with said cam surface means to secure said needle support element in locked assembly with said syringe body and being disengageable from said cam surface means for release of said needle support element for retraction thereof to said secured position.

13. The retractable hypodermic syringe of claim 11, wherein said cam means is moved linearly and rotationally by said plunger to positions of camming and locking engagement and disengagement relative to said cam surface means.

14. The retractable hypodermic syringe of claim 13, wherein:

(a) said cam surface means is defined by at least one arcuate tapered surface formed by said tubular needle connector of said syringe body, said tubular needle connector being located about said needle support passage; and (b) said cam projection extending radially from said needle support element and adapted for camming engagement with said cam surface means.

15. The retractable hypodermic syringe of claim 14, wherein:

said syringe body forms longitudinal cam passage means extending along said needle support passage and adapted to receive said cam projection means during linear movement of said needle support element through said needle support passage.

16. The retractable hypodermic syringe of claim 11, including:

(a) a first connector being defined by said needle support element; and (b) a second connector being defined by said plunger and adapted for releasable assembly with said first connector to secure said needle support element and said plunger in releasable assembly to thus permit linear and rotational movement of said needle support element by said plunger.

17. The retractable hypodermic syringe of claim 16, wherein:

(a) said first connector is a locking receptacle being formed within said needle support element; and (b) said second connector is a connector projection extending forwardly from said plunger and being receivable in locking engagement within said locking receptacle.

18. The retractable hypodermic syringe of claim 17, wherein:

(a) said locking receptacle forms a circular internal locking groove; and (b) said connector projection forming an external circular locking ridge being receivable in releasable locking engagement within said internal locking groove to secure said needle support element and said plunger in releasable assembly and to permit linear movement of said needle support element by said plunger.

19. The retractable hypodermic syringe of claim 11, wherein:

(a) said syringe barrel forms spaced internal ribs;

(b) said plunger defining a flexible flange being receivable in locked relation within the space between said spaced internal ribs and retaining the forward end of said plunger within said syringe barrel to thus secure said needle support element and a hypodermic needle supported thereby in completely enclosed protected relation within said syringe barrel.

20. The retractable hypodermic syringe of claim 19, wherein:

said plunger forms a frangible portion adjacent said flexible flange thus permitting the rear portion of said plunger to be broken away to render said syringe inoperative with said piston and needle support element secured in substantially immovable protected relation within said syringe barrel.

* * * * *